United States Patent
Madsen et al.

(10) Patent No.: US 10,745,661 B2
(45) Date of Patent: Aug. 18, 2020

(54) DRYING OF MICROORGANISMS

(71) Applicant: CHR. HANSEN A/S, Hoersholm (DK)

(72) Inventors: Michelle Madsen, Kirke Hyllinge (DK); Anders Clausen, Virum (DK)

(73) Assignee: CHR. HANSEN A/S, Hoersholm (DK)

( * ) Notice: Subject to any disclaimer, the term of this patent is extended or adjusted under 35 U.S.C. 154(b) by 671 days.

(21) Appl. No.: 15/031,591

(22) PCT Filed: Oct. 28, 2014

(86) PCT No.: PCT/EP2014/073128
§ 371 (c)(1),
(2) Date: Apr. 22, 2016

(87) PCT Pub. No.: WO2015/063090
PCT Pub. Date: May 7, 2015

(65) Prior Publication Data
US 2016/0257925 A1  Sep. 8, 2016

(30) Foreign Application Priority Data

Oct. 28, 2013 (DK) ................................ 2013 00612
Jan. 24, 2014 (DK) ................................ 2014 00044

(51) Int. Cl.
C12N 1/20 (2006.01)
B01J 2/04 (2006.01)
B01D 1/18 (2006.01)
F26B 3/12 (2006.01)
A23L 29/00 (2016.01)

(52) U.S. Cl.
CPC .............. *C12N 1/20* (2013.01); *A23L 29/065* (2016.08); *B01D 1/18* (2013.01); *B01J 2/04* (2013.01); *F26B 3/12* (2013.01)

(58) Field of Classification Search
None
See application file for complete search history.

(56) References Cited

U.S. PATENT DOCUMENTS

| 5,624,530 | A | * | 4/1997 | Sadykhov | ............ B01D 1/0082 159/23 |
| 6,010,725 | A | | 1/2000 | Meister et al. | |
| 7,037,708 | B1 | † | 5/2006 | Runge | |
| 2003/0138936 | A1 | * | 7/2003 | Mizuguchi | ............... C12N 1/04 435/252.31 |
| 2010/0189767 | A1 | † | 7/2010 | Shimoni | |
| 2013/0126102 | A1 | | 5/2013 | Kitamura et al. | |
| 2015/0218507 | A1 | | 8/2015 | Georgieva et al. | |
| 2017/0259185 | A1 | | 9/2017 | Madsen et al. | |

FOREIGN PATENT DOCUMENTS

| CN | 1616910 A | † | 5/2005 | |
| EP | 0 628 331 A1 | | 12/1994 | |
| EP | 0628331 A1 | * | 12/1994 | ............... B01D 1/18 |
| EP | 1 234 019 B1 | | 8/2002 | |
| EP | 1 281 752 A1 | | 2/2003 | |
| JP | H02-086766 A | | 3/1990 | |
| JP | H02-086767 A | | 3/1990 | |
| JP | H02-086768 A | | 3/1990 | |
| JP | 2010281523 A | * | 12/2010 | |
| NZ | 518826 A | | 11/2004 | |
| WO | WO-2008/035332 A1 | | 3/2008 | |
| WO | 2008046421 A1 | † | 4/2008 | |
| WO | WO-2008/088751 A2 | | 7/2008 | |
| WO | WO-2010/104713 A1 | | 9/2010 | |
| WO | WO2010104713 A1 | * | 9/2010 | ............... C22D 1/02 |
| WO | WO 2012/014923 A1 | | 2/2012 | |

OTHER PUBLICATIONS

Kim ("Survival of Lactic Acid Bacteria during Spray Drying of Plain Yogurt", Journal of Food Science, vol. 55, No. 4, 1990, 1008-1009 and 1048) (Year: 1990).*

Pispan ("Comparison of cell survival rates of *Escherichia coli* K12 and L. acidophilus undergoing spray drying", Food and Bioproducts Processing, 91 (2013), 362-369). (Year: 2013).*

"Spray drying"; Wikipedia, the free encyclopedia; [online] Retrieved on Sep. 12, 2015 from the Internet: <URL: https://en.wikipedia.org/wiki/Spray_drying> pp. 1-4.

Freitas, S., et al.; "Ultrasonic atomization into reduced pressure atmosphere-envisaging aseptic spray-drying for microencapsulation"; Journal of Controlled Release, vol. 95, No. 2; Mar. 5, 2004; pp. 185-195, Elsevier Ltd.

PCT International Search Report issued in application PCT/EP2014/073128 dated Sep. 9, 2015; 7 pages.

Semyonov, D., et al.; "Using ultrasonic vacuum spray dryer to produce highly viable dry probiotics"; LWT—Food Science and Technology, vol. 44, No. 9; Nov. 1, 2011; pp. 1844-1852; Elsevier Ltd.

Semyonov, David, et. al., Using ultrasonic vacuum spray dryer to produce highly viable dry probiotics, pp. 1844-1852, Nov. 2011, Elsevier Ltd., LWT—Food Science and Technology, vol. 44 (2011), Issue 9.†

Hoffman, Alex C., et al., Gas Cyclones and Swirl Tubes, p. 21, 2002, Springer Verlag Berlin Heidelberg (published 2002).†

* cited by examiner
† cited by third party

*Primary Examiner* — Robert J Yamasaki
*Assistant Examiner* — Charles Zoltan Constantine
(74) *Attorney, Agent, or Firm* — Foley & Lardner LLP

(57) ABSTRACT

The present invention relates to an improved method for drying microorganisms, especially lactic acid bacteria, in a spray dryer.

17 Claims, 1 Drawing Sheet

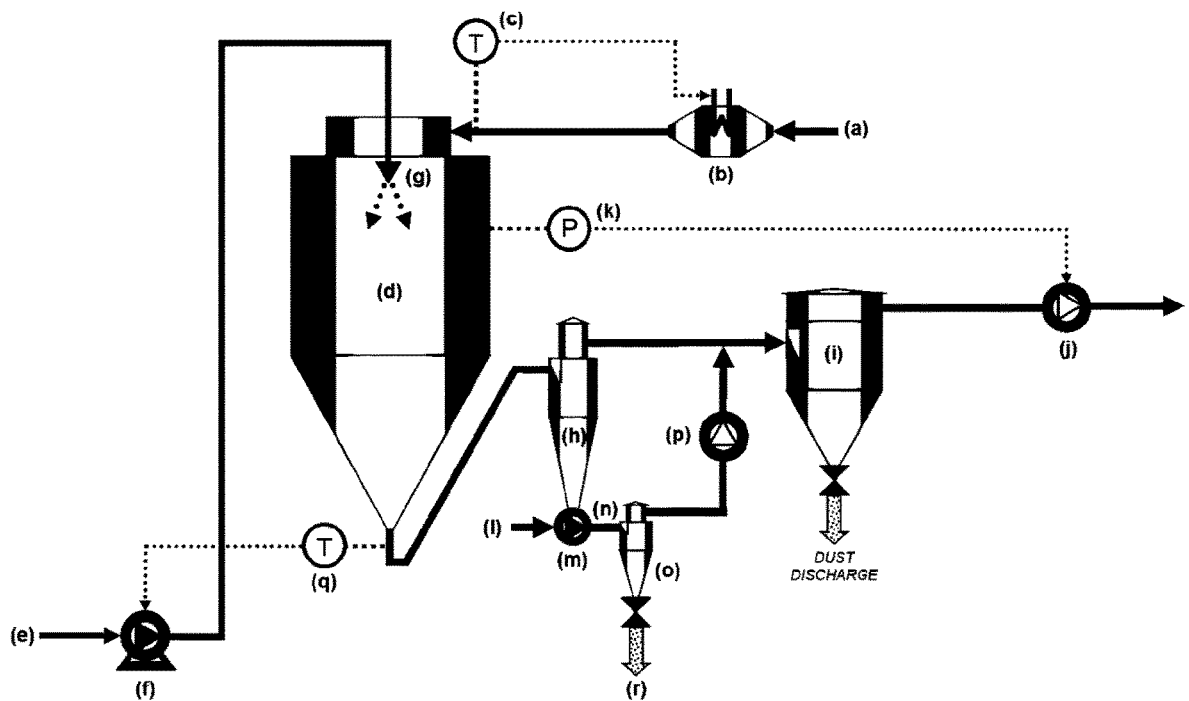

(a) Inert gas supply
(b) Inert gas heater
(c) Inlet temperature control loop
(d) Spray drying chamber
(e) Liquid feed supply
(f) Liquid feed pump
(g) Atomizer
(h) Primary cyclone
(i) Main fines separator (j) Primary exhaust fan
(k) Chamber pressure control loop
(l) Inert gas supply
(m) Venturi eductor
(n) Conveying line
(o) Secondary cyclone
(p) Secondary exhaust fan
(q) Outlet temperature control loop
(r) Powder discharge

DRYING OF MICROORGANISMS

FIELD OF INVENTION

The present invention relates to an improved method for drying a suspension containing e.g. microorganisms, especially lactic acid bacteria, in a spray dryer.

BACKGROUND OF INVENTION

Spray drying has previously been used for drying lactic acid bacteria, but without much commercial success.

For instance U.S. Pat. No. 6,010,725A (Nestle) relates to a process for spray drying microorganisms in a spray drying apparatus having an inlet temperature above 250° C. It is stated that at least 10% of the microorganisms survive the treatment.

SUMMARY OF INVENTION

Investigations have shown that in conventional spray drying of aqueous formulations at ambient atmospheric pressure, dryer outlet temperatures rarely go below 60° C. and if so only at throughput rates so low these drying methods do not offer an economical feasible alternative to for example freeze drying. And at such dryer outlet temperatures and higher will destroy and kill most LAB strains efficiently, as most bacteria living in the human gut (such as lactic acid bacteria—hereafter abbreviated LAB, especially anaerobic LAB) will not survive 40° C. for much time.

In an attempt to increase the survival of LAB during drying and to make spray drying an alternative to other methods for preservation, the present inventors tried to lower the pressure inside the spray dryer in order to lower the boiling point of water with the ambition to allow for dryer outlet temperatures in the range of 20°-50° C. By lowering the drying chamber pressure to say 65 kPa the boiling point of water would be reduced from 100° C. to 88° C., so this reduction should apply to the dryer outlet temperature too, meaning an economical feasible outlet temperature of say 87°-92° C. should produce fairly dry powders at 75°-80° C., which is still much too high for the bacteria to survive.

The inventors continued their work, and invented a new combination of drying methods capable of drying live lactic acid bacteria and at the same time yielding surprisingly high bacterial survival after drying.

To their surprise, they found it possible to produce dry powders using outlet temperatures in the range of 30°-60° C. with economical feasible throughput rates and with bacterial survival rates equal or superior to similar freeze dried LAB formulations. Lowering the drying pressure further to 5×10E4 Pa the boiling point of water will drop further to about 81° C. making it possible to spray dry at outlet temperatures in the range of 20°-50° C. which makes the method suitable for LAB.

The present inventors discovered that the best result was obtained when the drying gas used in spray dryer was free of oxygen, and we therefore contemplate that the gas should preferably be an inert gas like Nitrogen or any noble gas like Helium, Argon and Neon etc., but it could also be carbon dioxide or even methane.

In order to ensure good LAB survival, it is preferred to limit the time the LAB is exposed to temperatures above 20° C. Preferably, as soon as the spray dried powder is separated from the drying gas (eg by a cyclone separator) it should be cooled, such as to a temperature below 20° C., and/or by an inert conveying gas. The conveying cooling gas should preferable be dry with a dew point of at least −40° C. in order to allow for some degree of post-drying of the cooling powder during the conveying phase. The length of the conveying line influences the degree of post drying possible and allows for the cooled and post-dried LAB containing powder to be collected below a secondary cyclone separator (e.g. placed in suitable product discharge room) for packaging of the dried powder.

The best result is presently obtained by combining the use of an inert drying/conveying gas with drying pressures below ambient pressure and the use of cooling conveying gas immediately after the first cyclone separator.

The spray drying method of the invention results in improved survival of the LAB, and combined with the dryness of the produced LAB containing powders, and yields an economical feasible drying process for heat- and oxygen labile LAB containing products.

Further, it has turned out that the product of the drying process, ie the dried powder, has several unexpected advantages relative to a freeze dried product containing the same heat-labile material, e.g. improved survival (more active material, ie higher yield), easier applicability (the powder is easier to disperse in an aqueous solution such as milk).

The invention does not limit itself for LAB drying alone: Most live bacterial/viral strains, large macro-molecules like proteins/peptides and other biopharmaceutical/biological products in general will benefit from the low temperature drying method.

DETAILED DISCLOSURE

In a first aspect, the present invention relates to a process for removing liquid (e.g. water) from a solution or suspension comprising a heat-labile material, such as a protein or a microorganism, esp. a LAB, characterized in that:
a) the suspension or solution is sprayed into a gas (said gas preferably having an inlet temperature in the range from 100 to 200° C., or in the range 50 to 150° C. or 50 to 90° C. or 60 to 80° C.) in a spray dryer, the spray dryer having an outlet temperature of at most 70° C., and a pressure of at most 90 kPa (0.9 bar(a)); and
b) optionally the material (powder) resulting from step a) is removed (preferably continuously) from the spray dryer, so that the "dryer retention time" of the material is less than 20 minutes.

In the first aspect, the invention also relates to a process for removing liquid (e.g. water) from a solution or suspension comprising a heat-labile material, such as a protein or a microorganism, esp. a LAB, characterized in that:
a) the suspension or solution is sprayed into a gas (preferably having an inlet temperature in the range from 100 to 200° C.) in a spray dryer, the spray dryer having an outlet temperature of at most 70° C., and a pressure of at most 90 kPa (0.9 bar(a)); and
b) the material (powder) resulting from step a) is removed (preferably continuously) from the spray dryer, so that the "dryer retention time" of the material is less than 20 minutes in the spray dryer.

In the first aspect, the invention further relates to a process for drying a microorganism (esp. a LAB) containing suspension, characterized in that:
a) an aqueous suspension containing microorganisms (preferably having a concentration of at least 1.0E+8 microorganisms per ml) is sprayed into a gas (preferably having an inlet temperature in the range from 100 to 200° C.) in a spray dryer, the spray dryer having an outlet temperature of at most 70° C., and a pressure of at most 90 kPa (0.9 bar(a)); and b) optionally the material (powder) resulting from the drying step a) is removed (preferably continuously) from the spray dryer, so that the "dryer retention time" of the material is less than 20 minutes.

Yet an embodiment of first aspect relates to a process for drying a microorganism (esp. LAB (Lactic Acid Bacteria)) containing aqueous (or liquid) suspension, comprising the following steps:

a) Contacting droplets of the suspension containing the microorganisms (said droplets preferably having a size from 10 to 500 micrometer, such as a size in the ranges: 15 to 400, 20 to 350, 50 to 350, 100 to 350, 20 to 300, 20 to 200, 50 to 300, 50 to 200, 100 to 300, or 100 to 200, measured as the Dv50 value in microns (Dv50 is defined as the maximum particle diameter below which 50% of sample volume exists, according to the ISO 13320:2009 standard for "Particle size analysis—Laser diffraction methods") and e.g. obtained by spraying (atomizing) the suspension) with a drying gas (preferably having a temperature in the range from 20° C. to 250° C., and/or preferably for a time period of from 1 second to 120 seconds); and b) Removing (preferably continuously) the material (powder) from step a), eg by means of a cyclone and/or eg so the materials retention time in the drying apparatus is less than 20 minutes;

c) optionally subjecting the resulting product from step b) to a further drying step, such as drying under reduced pressure, e.g. freeze-drying; and d) optionally packaging the resulting product, such as in an air-tight and/or moisture-tight package (optionally together with microorganisms of a different strain).

Preferably the above process step a) is carried out in a spray dryer having an outlet temperature of at most 70° C., and/or a pressure of at most 90 kPa (0.9 bar(a)).

A special embodiment the invention in the first aspect relates to a process for drying a microorganism (esp. a LAB) containing suspension, characterized in that:

a) an aqueous suspension (having a concentration of at least 1.0E+8 microorganisms per ml) is sprayed into a gas (preferably having an inlet temperature in the range from 100 to 200° C.) in a spray dryer, the spray dryer having an outlet temperature of at most 70° C., and a pressure of at most 90 kPa (0.9 bar(a)); and b) the powder resulting from the drying step a) is removed (preferably continuously) from the spray dryer, so that the "dryer retention time" of the dried powder is less than 20 minutes in the spray dryer.

Interesting embodiments of the processes of the first aspect of the invention are:

A process wherein step b) is performed immediately after step a), eg by means of a cyclone which is able to separate the material from the gas.

A process, wherein the material (powder) from step b) is cooled, e.g. to a temperature below 40° C., preferably immediately after removal from the spray drier or the unit operation separating the dried powder from the gas.

A process, wherein the "dryer retention time" of the dried powder is less than 2 minutes in the spray dryer.

A process, characterized in that step a) is carried out at a gas outlet temperature of at most 60° C., advantageously between 10° C. and 50° C. and more preferably between 20° C. and 50° C.

A process, characterized in that step a) is carried out at a hot-gas inlet temperature of at most 500° C., advantageously between 80° C. and 200° C. and more preferably between 80° C. and 160° C.

A process wherein step a) is carried out at a hot gas inlet temperature in the range from 100 to 200° C., or in the range from 100 to 150° C. or in the range from 80 to 160 or in the range 50 to 150° C. or in the range from 50 to 90° C. or or in the range from 60 to 80° C.

A process, characterized in that after the drying step a) the powder has a particle size of between 1 and 200 microns and preferably between 5 and 100 microns.

A process characterized in that after the drying step a) the powder has a particle size of between 1 and 200 microns and preferably between 5 and 100 microns, measured as the Dv50 value.

A process, characterized in that the drying step takes place under a reduced pressure of between 15 and 80 kPa, preferably between 30 and 70 kPa.

A process, characterized in that the drying step takes place under a pressure of between 40 and 85 kPa, preferably between 50 and 75 kPa.

A process, characterized in that the drying step takes place at a temperature of between 10 and 60° C., preferably between 20 and 50° C.

A process, wherein the duration of the drying step is a time suitable for obtaining a powder whose residual water content is at less than 20 percent by weight with respect to the total weight of the powder.

A process, characterized in that the powder resulting from the drying step a) possesses a residual water content of between 0 and 15 percent by weight, and preferably between 5 and 15 percent by weight, more preferable between 5 and 12 percent by weight, with respect to the total weight of the powder.

A process, wherein the duration of the drying step is a time suitable for obtaining a powder whose residual water content of the powder is at least 0.05.

A process, wherein the gas contains less than 5% oxygen, such as less than 2%.

A process, wherein the gas is selected from the group consisting of an inert gas (such as Nitrogen), a noble gas (such as Helium, Argon or Neon) etc., carbon dioxide, and an alkane gas (such methane), and a mixture thereof.

A process, wherein the gas has (an inlet) temperature in the range from 100 to 150° C. or in the range from 80 to 160° C.

A process, wherein the solution or suspension further comprises an additive that stabilizes the material/microorganism.

A process, wherein the additive is selected from the group consisting of: maltodextrin, trehalose, inositol, sucrose, skim milk powder (SMP), lactose, casein peptone, casein, potato protein peptone, and yeast extract.

A process wherein the additive is selected from the group consisting of: inulin, polysorbate, inosine, inosinemonophosphate, glutaminate, caseinate, and ascorbate.

A process, wherein the ratio heat labile material:additive is within the range from 1:0.5 to 1:5, such as from 1:1 to 1:4 or from 1:1½ to 1:3, (w/w of the dry weights).

A process, wherein the ratio heat labile material:additive is within the range from 1:0.5 to 1:5, such as from 1:1 to 1:4 or from 1:1½ to 1:3, (based on dry matter content weight:weight).

A process, wherein the microorganism is selected from the group consisting of: a yeast (eg *Saccharomyces*), a *Streptococcus* species, a *Lactobacillus* species, a *Lactococcus* species, a *Leuconostoc* species, a *Bifidobacterium* Species, an *Oenococcus* species, a *Bacillus* species.

A process, wherein the microorganism is selected from the group consisting of: *Lactococcus lactis* subsp. *lactis, Lactococcus lactis* subsp. *cremoris, Leuconostoc mesenteroides* subsp. *cremoris, Pediococcus pentosaceus, Lactococcus lactis* subsp. *lactis biovar. diacetylactis Lactobacillus casei* subsp. *Casei, Streptococcus thermophilus, Enterococcus faecium, Lactobacillus lactis, Lactobacillus helveticus, Lactobacillus delbrueckii* subsp. *bulgaricus* and *Lactobacillus acidophilus*.

A process, wherein the microorganism is selected from the group consisting of *Streptococci* species (such as *Streptococcus thermophilus*), and the outlet temperature is in the range of 25-65° C. (such as in the range 25-35° C.), and the pressure in the drying unit is in the range 20 to 80 kPa.

A process, wherein the microorganism is selected from the group consisting of *Bifidobacterium* species (such as *Bifidobacterium longum* or *Bifidobacterium animalis* ssp. *Lactis*), and the outlet temperature is in the range 35-65° C., and the pressure in the drying unit is in the range 30 to 90 kPa.

A process, wherein the microorganism is selected from the group consisting of *Lactobacillus* species (such as *Lactobacillus casei* or *Lactobacillus acidophilus*), and the outlet temperature is in the range 35-65° C., and the pressure in the drying unit is in the range 30 to 90 kPa.

A process, wherein the microorganism is selected from the group consisting of *Lactococcus* species (such as *Lactococcus lactis* subsp. *Lactis* or *Lactococcus lactis* subsp. *Cremoris*), and the outlet temperature is in the range 35-65° C., and the pressure in the drying unit is in the range 30 to 90 kPa.

A process, wherein the microorganism is selected from the group consisting of *Bacillus* species (such as *Bacillus subtilis*), and the outlet temperature is in the range 35-65° C., and the pressure in the drying unit is in the range 40 to 90 kPa.

A process, wherein the microorganism is selected from the group consisting of *Streptococci* species, and the outlet temperature is in the range 25-65° C. (such as in the range 25-35° C.), and the pressure in the drying unit is in the range 40 to 60 kPa.

A process, wherein the microorganism is selected from the group consisting of *Bifidobacterium* species, and the outlet temperature is in the range 35-65° C., and the pressure in the drying unit is in the range 60 to 90 kPa.

A process, wherein the microorganism is selected from the group consisting of *Lactobacillus* species, and the outlet temperature is in the range 35-65° C., and the pressure in the drying unit is in the range 60 to 90 kPa.

A process, wherein the microorganism is selected from the group consisting of *Lactococcus* species, and the outlet temperature is in the range 35-65° C., and the pressure in the drying unit is in the range 60 to 90 kPa.

A process, wherein the microorganism is selected from the group consisting of *Bacillus* species, and the outlet temperature is in the range 35-65° C., and the pressure in the drying unit is in the range 70 to 90 kPa.

A process wherein the material from step b) is conveyed to a separator (such as a cyclone) by means of a cooling gas (such as a gas having a temperature below 50° C. or below 30° C., below 20° C., such as in the range 5 to 25° C.

A process wherein the cooling gas contains less than 5% oxygen, such as less than 2%.

A process wherein the cooling gas is selected from the group consisting of an inert gas (such as Nitrogen), a noble gas (such as Helium, Argon or Neon) etc., carbon dioxide, and an alkane gas (such methane), and a mixture thereof.

In a second aspect, the present invention relates to a product obtainable by the process of any preceding claim, such as a dried protein or microorganism. The product is preferably packaged (e.g. in an airtight container) without performing any further drying unit operation, such as freeze drying.

In a final aspect, the present invention relates to an apparatus or equipment usable in the process of any preceding claim, such as an apparatus substantially as depicted on FIG. 1.

In its simplest embodiment, the apparatus of the invention comprises a spray dryer, a first separator (eg cyclone) coupled to the spray dryer, and a second separator (eg cyclone) coupled to the first separator (eg cyclone). More specific, the apparatus may comprise a spray dryer, a first separator (eg cyclone) coupled to the material outlet of the spray dryer, and a second separator (eg cyclone) coupled to the material outlet of the first separator (eg cyclone). It should be understood that a preferred apparatus has the first cyclone linked to the spray dryer in such a way that the dried material will be conveyed from the spray dryer to the first cyclone where the gas is separated from the dried material. The second cyclone is linked to the first cyclone is such a way the the material from the first cyclone can be conveyed to the second cyclone. Most interesting, the apparatus comprises an gas inlet between the first cyclone and the second cyclone, so that the gas will convey the material discharged from the first cyclone to the second cyclone. The dried material may by discharged from the second cyclone and further processed, e.g. cooled, packaged, freeze dried, etc. Preferably the gas is a cooling gas (such as a gas having a temperature below 50° C., below 30° C., or below 20° C.), preferably a the cooling gas contains less than 5% oxygen, such as less than 2%. The cooling gas may be selected from the group consisting of an inert gas (such as Nitrogen), a noble gas (such as Helium, Argon or Neon) etc., carbon dioxide, and an alkane gas (such methane), and a mixture thereof.

In a present preferred embodiment, the following process equipment is used as described, cf. FIG. 1.

(a) Primary inert gas supply
(b) Primary inert gas heater
(c) Inlet temperature control loop
(d) Spray drying chamber,
(e) Liquid feed supply
(f) Liquid feed pump
(g) Atomization device
(h) Primary cyclone separator
(i) Main fines separator
(j) Primary exhaust fan
(k) Chamber pressure control loop
(l) Secondary inert gas supply
(m) Venturi eductor -continued (n) Cooling conveying line
(o) Secondary cyclone separator
(p) Secondary exhaust fan
(q) Outlet temperature control loop
(r) Dry powder discharge A primary inert gas supply (a) is connected to the inlet of a gas heater (b). The gas heater is connected to the spray drying chamber top inlet (d) and heats the inert gas to an the inlet temperature set by the inlet control loop (c).

The liquid feed supply (e) is connected to the suction side of a liquid feed pump (f) which pumps the liquid formulation to the atomization device (g) on the top of the spray drying chamber (d). The atomization device (g) sprays the liquid feed into a cloud of aerosol droplets which dries into particles by consuming the heat supplied by the heated inert gas.

The spray dried particles leaves the spray dryer bottom outlet (d) together with the now cooled and moist inert gas towards the primary cyclone separator (h) where the spray dried particles are separated from the inert gas. The cooled and moist inert gas is led to the main fines separator (i) and downstream a primary exhaust fan (j) creates the required vacuum set by the chamber pressure control loop (k).

Below the primary cyclone separator (h) the secondary inert gas supply (l) is connected to a venturi eductor (m), which use the secondary inert gas to convey the spray dried powder towards a secondary cyclone separator (o) via a conveying line (n) of variable length. Below the secondary cyclone separator (o) the cooled and post-dried powder is discharged and recovered. The secondary inert gas leaving the secondary cyclone separator (o) is led to the secondary exhaust fan (p) and from here to the inlet of the main fines separator (i).

To improve the control of the drying chamber outlet temperature an outlet temperature control loop (q) is used to control the liquid feed pump (f).

Definitions

As used herein, the term "lactic acid bacterium" (LAB) designates a gram-positive, microaerophilic or anaerobic bacterium, which ferments sugars with the production of acids including lactic acid as the predominantly produced acid, acetic acid and propionic acid. The industrially most useful lactic acid bacteria are found within the order "Lactobacillales" which includes *Lactococcus* spp., *Streptococcus* spp., *Lactobacillus* spp., *Leuconostoc* spp., *Pseudoleuconostoc* spp., *Pediococcus* spp., *Brevibacterium* spp., *Enterococcus* spp. and *Propionibacterium* spp. Additionally, lactic acid producing bacteria belonging to the group of the strict anaerobic bacteria, bifidobacteria, i.e. *Bifidobacterium* spp., are generally included in the group of lactic acid bacteria. These are frequently used as food cultures alone or in combination with other lactic acid bacteria. Interesting species of LAB are selected from the group comprising the strains of the species and subspecies *Bifidobacterium bifidum, Bifidobacterium lactis, Bifidobacterium longum, Bifidobacterium breve, Bifidobacterium animalis* ssp. *Lactis, Lactobacillus reuteri, Lactobacillus acidophilus, Lactobacillus casei, Lactobacillus plantarum, Lactobacillus delbruckii bulgaricus, Lactobacillus rhamnosus, Streptococcus thermophilus, Lactococcus lactis, Lactobacillus pentoceus, Lactobacillus buchneri, Lactobacillus brevis, Pediococcus pentosaceus, Pediococcus acidilactici, Pediococcus pervulus, Propionibacterium freudenreichi, Propionibacterium jenseni, Lactococcus lactis, Streptococcus salivarius, Streptococcus thermophilus* and mixtures thereof.

Also the term LAB includes the strains *Lactobacillus rhamnosus* GG (LGG®), *Lactobacillus casei* (*L. casei* 431®), *Lactococcus lactis* (R704), *Bifidobacterium animalis* ssp. *Lactis* (BB-12®), *Streptococcus thermophilus* (ST-Fe 2), *Lactobacillus bulgaricus* (LB CH-2)

In the present context, the term "packaging" (a suitable amount of) the dried microorganism in a suitable package relates to the final packaging to obtain a product that can be shipped to a customer. A suitable package may thus be a container, bottle or similar, and a suitable amount may be e.g. 1 g to 30000 g, but it is presently preferred that the amount in a package is from 50 g to 10000 g. In case of eg probiotics, the package size may be smaller, from 0.1 g to 5 g. The term package includes a bag, a box, a capsule, a pouch, a sachet, a container, etc.

The term "dryer retention time" is to be understood as the time wherein the particles are subjected to drying conditions such as being exposed to drying gas and/or elevated temperature. In context of the preferred apparatus of the present invention the term may be understood as the time until the particles are discharged from the second cyclone.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

DRAWING

FIG. 1 depicts a preferred spray drying equipment that can be used according to the invention

EXPERIMENTAL

Example 1

A sample of 750 g of *Lactobacillus rhamnosus* GG (LGG®) concentrate was kept at <5° C. This contained 8E+11 CFU/g with approx. 10% (w/w) dry solids and to this was added under agitation: 450 g trehalose dihydrate, 200 g Glucidex (Maltodextrin 12 DE), 75 g inulin and 25 g sodium ascorbate. This resulted in 1.5 kg of liquid formulation with approx. 51% (w/w) dry solids to be spray dried. This liquid formulation contained now approx. 4.0E+11 CFU/g and was kept cold (<5° C.) throughout the test.

A GEA Niro Mobile Minor laboratory spray dryer was used for the spray drying. The spray dryer was supplied with pure nitrogen and connected to a vacuum source capable of creating a vacuum of −0.33 Bar(g), ie a pressure of 0.67 bar in the spray dryer. The spray dryer inlet temperature was kept at 65-66° C., using a nitrogen drying gas kept at a mass flow-rate of approx. 80 kg/h. The spray dryer outlet temperature was adjusted with pure water to about 35° C., before switching to the above mentioned formulation. A 2-fluid nozzle (Schlick 0-2) was used for the atomization, using an atomization gas flow of approx. 6 kg/h (Nitrogen) equivalent to an atomization pressure of 0.9 Bar(g). After switching from pure water to the above formulation a liquid feed-rate was kept at 1.28 kg/h and the spray dryer outlet temperature was kept at 38-39° C.

A free-flowing powder with an average particle size of 16 micron was collected below the secondary cyclone after being cooled by the conveying gas to about 20° C. After 1 hour and 10 min. about 747 g of spray dried formulation had been collected, which corresponds to a yield of about 90%. The moisture content was 7.5% (w/w) measured as total volatiles on a Sartorious IR at 115° C. The equivalent water activity was about 0.39 at 24° C.

The obtained spray dried powders contained 2.0E+11 CFU/g ±15%, equivalent to a survival rate of about 27%, compared to <0.1% when drying the same formulation on the same spray dryer at ambient pressure in air and with no cooling conveying gas. Samples were taken for accelerated stability at 35° C./30% RH and after one week the powders contained 1.5E+11 CFU/g, after 2 weeks 1E+11 CFU/g and after 3 weeks the powders contained 8E+10 CFU/g.

EXAMPLE 2

A sample of 500 g of *Lactobacillus casei* (*L. casei* 431®) concentrate was kept at <5° C. This contained 1.2E+11 CFU/g with approx. 12.5% (w/w) dry solids. Parallel to this 1500 g of solution was prepared by adding the following ingredients to 1000 g of cold tap water (approx. 10° C.) under agitation: 375 g trehalose dihydrate, 85 g casein peptone, 25 g inulin and 15 g sodium alginate. This resulted in 2 kg of liquid formulation with approx. 26% (w/w) dry solids to be spray dried. This liquid formulation contained now approx. 3.0E+10 CFU/g and was kept cold (<5° C.) throughout the test.

A GEA Niro Mobile Minor laboratory spray dryer was used for the spray drying. The spray dryer was supplied with pure nitrogen and connected to a vacuum source capable of creating a vacuum of −0.33 Bar(g). The spray dryer inlet temperature was kept at 65-66° C., using a nitrogen drying gas kept at a mass flow-rate of approx. 80 kg/h. The spray dryer outlet temperature was adjusted with pure water to about 36° C., before switching to the above mentioned formulation. A 2-fluid nozzle (Schlick 0-2) was used for the atomization, using an atomization gas flow of approx. 7 kg/h (Nitrogen) equivalent to an atomization pressure of 1 Bar(g). After switching from pure water to the above formulation a liquid feed-rate was kept at 1.0 kg/h and the spray dryer outlet temperature was kept at 39-40° C.

A free-flowing powder was collected below the secondary cyclone after being cooled by the conveying gas to about 20° C. After 2 hours in total about 576 g of spray dried formulation had been collected, which corresponds to a yield of about 93%. The moisture content was 5.8% (w/w) measured as total volatiles on a Sartorious IR at 115° C. The equivalent water activity was about 0.31 at 24° C. The obtained spray dried powder contained 2.8E+10 CFU/g ±15%, equivalent to a survival rate of 26%, compared to a survival rate of <0.1% when drying the same formulation on the same spray dryer at ambient pressure in air and with no cooling conveying gas.

EXAMPLE 3

A sample of 1000 g of *Lactococcus lactis* (R704) concentrate was kept at <5° C. This contained 8.5E+11 CFU/g with approx. 16.5% (w/w) dry solids. Parallel to this 1000 g of solution was prepared by adding the following ingredients to 730 g of cold tap water (approx. 10° C.) under agitation: 115 g Glucidex (Maltodextrin 12 DE), 50 g sodium ascorbate, 50 g lactose monohydrate, 25 g sodium caseinate, 15 g inositol and 15 g monosodium glutamate (MSG). This resulted in 2 kg of liquid formulation with approx. 22% (w/w) dry solids to be spray dried. This liquid formulation contained now approx. 4.2E+11 CFU/g and was kept cold (<5° C.) throughout the test.

A GEA Niro Mobile Minor laboratory spray dryer was used for the spray drying. The spray dryer was supplied with pure nitrogen and connected to a vacuum source capable of creating a vacuum of −0.36 Bar(g). The spray dryer inlet temperature was kept at 70-71° C., using a nitrogen drying gas kept at a mass flow-rate of approx. 80 kg/h. The spray dryer outlet temperature was adjusted with pure water to about 32° C., before switching to the above mentioned formulation. A 2-fluid nozzle (Schlick 0-2) was used for the atomization, using an atomization gas flow of approx. 7 kg/h (Nitrogen) equivalent to an atomization pressure of 1 Bar(g). After switching from pure water to the above formulation a liquid feed-rate was kept at 1.05 kg/h and the spray dryer outlet temperature was kept at 35-36° C.

A free-flowing powder was collected below the secondary cyclone after being cooled by the conveying gas to about 20° C. After 1 hour and 55 min. about 418 g of spray dried formulation had been collected, which corresponds to a yield of about 91%. The moisture content was 5.1% (w/w) measured as total volatiles on a Sartorious IR at 115° C. The equivalent water activity was about 0.29 at 23° C. The obtained spray dried powder contained 6.0E+11 CFU/g ±15%, equivalent to a survival rate of 31%, compared to <0.1% when drying the same formulation on the same spray dryer at ambient pressure in air and with no cooling conveying gas.

EXAMPLE 4

A sample of 2000 g of *Bifidobacterium animalis* ssp. *Lactis* (BB-12®) concentrate was kept at <5° C. This contained 1.05E+11 CFU/g with approx. 12.5% (w/w) dry solids. Parallel to this 1000 g of solution was prepared by adding the following ingredients to 635 g of cold tap water (approx. 10° C.) under agitation: 140 g Glucidex (Maltodextrin 12 DE), 70 g sodium ascorbate, 55 g skimmed milk powder, 50 g lactose monohydrate, 25 g inositol and 25 g monosodium glutamate (MSG). This resulted in 3 kg of liquid formulation with approx. 20% (w/w) dry solids to be spray dried. This liquid formulation contained now approx. 7E+10 CFU/g and was kept cold (<5° C.) throughout the test.

A GEA Niro Mobile Minor laboratory spray dryer was used for the spray drying. The spray dryer was supplied with pure nitrogen and connected to a vacuum source capable of creating a vacuum of −0.39 Bar(g). The spray dryer inlet temperature was kept at 70-71° C., using a nitrogen drying gas kept at a mass flow-rate of approx. 80 kg/h. The spray dryer outlet temperature was adjusted with pure water to about 32° C., before switching to the above mentioned formulation. A 2-fluid nozzle (Schlick 0-2) was used for the atomization, using an atomization gas flow of approx. 7 kg/h (Nitrogen) equivalent to an atomization pressure of 1 Bar(g). After switching from pure water to the above formulation a liquid feed-rate was kept at 1.5 kg/h and the spray dryer outlet temperature was kept at 35-36° C.

A free-flowing powder was collected below the secondary cyclone after being cooled by the conveying gas to about 20° C. After 2 hours about 589 g of spray dried formulation had been collected, which corresponds to a yield of about 90%. The moisture content was 9.1% (w/w) measured as total volatiles on a Sartorious IR at 115° C. The equivalent water activity was about 0.27 at 24° C. The obtained spray dried powder contained 3.4E+11 CFU/g ±15%, equivalent to a survival rate of 71%, compared to <0.1% when drying the same formulation on the same spray dryer at ambient pressure in air and with no cooling conveying gas. After 4 months at approx. 25° C./27% RH the powder contained about 3.4E+10 CFU/g.

EXAMPLE 5

A sample of 1000 g of *Streptococcus thermophilus* (ST-Fe 2) concentrate was kept at <5° C. This contained 1.6E+12 CFU/g with approx. 14.6% (w/w) dry solids. Parallel to this 1000 g of solution was prepared by adding the following ingredients to 550 g of cold tap water (approx. 10° C.) under agitation: 225 g Glucidex (Maltodextrin 12 DE), 100 g lactose monohydrate, 70 g sodium ascorbate, 25 g sodium caseinate, 15 g inositol and 15 g monosodium glutamate (MSG). This resulted in 2 kg of liquid formulation with approx. 28.9% (w/w) dry solids to be spray dried. This liquid formulation contained now approx. 8E+11 CFU/g and was kept cold (<5° C.) throughout the test.

A GEA Niro Mobile Minor laboratory spray dryer was used for the spray drying. The spray dryer was supplied with pure nitrogen and connected to a vacuum source capable of creating a vacuum of −0.38 Bar(g). The spray dryer inlet temperature was kept at 70-71° C., using a nitrogen drying gas kept at a mass flow-rate of approx. 80 kg/h. The spray dryer outlet temperature was adjusted with pure water to about 32° C., before switching to the above mentioned formulation. A 2-fluid nozzle (Schlick 0-2) was used for the atomization, using an atomization gas flow of approx. 7 kg/h (Nitrogen) equivalent to an atomization pressure of 1 Bar(g). After switching from pure water to the above formulation a liquid feed-rate was kept at 1.7 kg/h and the spray dryer outlet temperature was kept at 35-36° C.

A free-flowing powder was collected below the secondary cyclone after being cooled by the conveying gas to about 20° C. After 1 hour and 12 min. about 558 g of spray dried formulation had been collected, which corresponds to a yield of about 91%. The moisture content was 6.1% (w/w) measured as total volatiles on a Sartorious IR at 115° C. The equivalent water activity was about 0.37 at 25° C. The obtained spray dried powder contained 1.2E+11 CFU/g ±15%, equivalent to a survival rate of 25%, compared to <0.1% when drying the same formulation on the same spray dryer at ambient pressure in air and with no cooling conveying gas.

EXAMPLE 6

A sample of 500 g of *Lactobacillus bulgaricus* (LB CH-2) concentrate was kept at <5° C. This contained 1.2E+11 CFU/g with approx. 11.5% (w/w) dry solids. Parallel to this 1000 g of solution was prepared by adding the following ingredients to 630 g of cold tap water (approx. 10° C.) under agitation: 174 g Glucidex (Maltodextrin 12 DE), 115 g lactose monohydrate, 50 g sodium ascorbate, 17 g skimmed milk powder, 7 g inositol and 7 g monosodium glutamate (MSG). This resulted in 1.5 kg of liquid formulation with approx. 27.5% (w/w) dry solids to be spray dried. This liquid formulation contained now approx. 4E+10 CFU/gram and was kept cold (<5° C.) throughout the test.

A GEA Niro Mobile Minor laboratory spray dryer was used for the spray drying. The spray dryer was supplied with pure nitrogen and connected to a vacuum source capable of creating a vacuum of −0.38 Bar(g). The spray dryer inlet temperature was kept at 70-71° C., using a nitrogen drying gas kept at a mass flow-rate of approx. 80 kg/h. The spray dryer outlet temperature was adjusted with pure water to about 32° C., before switching to the above mentioned formulation. A 2-fluid nozzle (Schlick 0-2) was used for the atomization, using an atomization gas flow of approx. 7 kg/h (Nitrogen) equivalent to an atomization pressure of 1 Bar(g). After switching from pure water to the above formulation a liquid feed-rate was kept at 1.5 kg/h and the spray dryer outlet temperature was kept at 35-36° C.

A free-flowing powder was collected below the secondary cyclone after being cooled by the conveying gas to about 20° C. After 1 hour about 347 g of spray dried formulation had been collected, which corresponds to a yield of about 76%. The moisture content was 10.8% (w/w) measured as total volatiles on a Sartorious IR at 115° C. The equivalent water activity was about 0.42 at 25° C. The obtained spray dried powder contained 1.9E+09 CFU/g ±15%, equivalent to a survival rate of 15.5%, compared to a survival rate of <0.1% when drying the same formulation on the same spray dryer at ambient pressure in air and with no cooling conveying gas.

EXAMPLE 7

A sample of 1000 g of *Lactococcus lactis* (R704) concentrate was kept at <5° C. This contained 8.5E+11 CFU/g with approx. 16.5% (w/w) dry solids. Parallel to this 1000 g of solution was prepared by adding the following ingredients to 730 g of cold tap water (approx. 10° C.) under agitation: 115 g Glucidex (Maltodextrin 12 DE), 50 g sodium ascorbate, 50 g lactose, monohydrate, 25 g sodium caseinate, 15 g inositol and 15 g monosodium glutamate (MSG). This resulted in 2 kg of liquid formulation with approx. 22%

(w/w) dry solids to be spray dried. This liquid formulation contained now approx. 4.2E+11 CFU/g and was kept cold (<5° C.) throughout the test.

A GEA Niro Mobile Minor laboratory spray dryer was used for the spray drying. The spray dryer was supplied with pure nitrogen and connected to a vacuum source capable of creating a vacuum of −0.36 Bar(g). The spray dryer inlet temperature was kept at 100-101° C., using a nitrogen drying gas kept at a mass flow-rate of approx. 80 kg/h. The spray dryer outlet temperature was adjusted with pure water to about 42° C., before switching to the above mentioned formulation. A 2-fluid nozzle (Schlick 0-2) was used for the atomization, using an atomization gas flow of approx. 7 kg/h (Nitrogen) equivalent to an atomization pressure of 1 Bar(g). After switching from pure water to the above formulation a liquid feed-rate was kept at 1.05 kg/h and the spray dryer outlet temperature was kept at 45-46° C.

A free-flowing powder was collected below the secondary cyclone after being cooled by the conveying gas to about 20° C. After 1 hour and 55 min. about 418 g of spray dried formulation had been collected, corresponding to a yield of 91%. The moisture content was 5.1% (w/w) measured as total volatiles on a Sartorious IR at 115° C. The equivalent water activity was about 0.21 at 23° C. The obtained spray dried powder contained 6.0E+11 CFU/g ±15%, equivalent to a survival rate of 31%, compared to <0.1% when drying the same formulation on the same spray dryer at ambient pressure in air and with no cooling conveying gas.

EXAMPLE 8

A sample of 2000 g of *Bifidobacterium animalis* ssp. *Lactis* (BB-12®) concentrate was kept at <5° C. This contained 1.05E+11 CFU/g with approx. 12.5% (w/w) dry solids. Parallel to this 1000 g of solution was prepared by adding the following ingredients to 635 g of cold tap water (approx. 10° C.) under agitation: 140 g Glucidex (Maltodextrin 12 DE), 70 g sodium ascorbate, 55 g skimmed milk powder, 50 g lactose monohydrate, 25 g inositol and 25 g monosodium glutamate (MSG). This resulted in 3 kg of liquid formulation with approx. 20% (w/w) dry solids to be spray dried. This liquid formulation contained now approx. 7E+10 CFU/g and was kept cold (<5° C.) throughout the test.

A GEA Niro Mobile Minor laboratory spray dryer was used for the spray drying. The spray dryer was supplied with pure nitrogen and connected to a vacuum source capable of creating a vacuum of −0.39 Bar(g). The spray dryer inlet temperature was kept at 120-121° C., using a nitrogen drying gas kept at a mass flow-rate of approx. 80 kg/h. The spray dryer outlet temperature was adjusted with pure water to about 52° C., before switching to the above mentioned formulation. A 2-fluid nozzle (Schlick 0-2) was used for the atomization, using an atomization gas flow of approx. 7 kg/h (Nitrogen) equivalent to an atomization pressure of 1 Bar(g). After switching from pure water to the above formulation a liquid feed-rate was kept at 1.5 kg/h and the spray dryer outlet temperature was kept at 55-56° C.

A free-flowing powder was collected below the secondary cyclone after being cooled by the conveying gas to about 20° C. After 2 hours about 589 g of spray dried formulation had been collected, corresponding to a yield of 90%. The moisture content was 9.1% (w/w) measured as total volatiles on a Sartorious IR at 115° C. The equivalent water activity was about 0.15 at 24° C. The obtained spray dried powder contained 3.4E+11 CFU/g ±15%, equivalent to a survival rate of 71%, compared to <0.1% when drying the same formulation on the same spray dryer at ambient pressure in air and with no cooling conveying gas. After 4 months at approx. 25° C./27% RH the powder contained about 3.4E+10 CFU/g.

EXAMPLE 9

A sample of 1000 g of *Streptococcus thermophilus* (ST-Fe 2) concentrate was kept at <5° C. This contained 1.6E+12 CFU/g with approx. 14.6% (w/w) dry solids. Parallel to this 1000 g of solution was prepared by adding the following ingredients to 550 g of cold tap water (approx. 10° C.) under agitation: 225 g Glucidex (Maltodextrin 12 DE), 100 g lactose monohydrate, 70 g sodium ascorbate, 25 g sodium caseinate, 15 g inositol and 15 g monosodium glutamate (MSG). This resulted in 2 kg of liquid formulation with approx. 28.9% (w/w) dry solids to be spray dried. This liquid formulation contained now approx. 8E+11 CFU/g and was kept cold (<5° C.) throughout the test.

A GEA Niro Mobile Minor laboratory spray dryer was used for the spray drying. The spray dryer was supplied with pure nitrogen and connected to a vacuum source capable of creating a vacuum of −0.38 Bar(g). The spray dryer inlet temperature was kept at 90-91° C., using a nitrogen drying gas kept at a mass flow-rate of approx. 80 kg/h. The spray dryer outlet temperature was adjusted with pure water to about 42° C., before switching to the above mentioned formulation. A 2-fluid nozzle (Schlick 0-2) was used for the atomization, using an atomization gas flow of approx. 7 kg/h (Nitrogen) equivalent to an atomization pressure of 1 Bar(g). After switching from pure water to the above formulation a liquid feed-rate was kept at 1.7 kg/h and the spray dryer outlet temperature was kept at 45-46° C.

A free-flowing powder was collected below the secondary cyclone after being cooled by the conveying gas to about 20° C. After 1 hour and 12 min. about 558 g of spray dried formulation had been collected, corresponding to a yield of about 91%. The moisture content was 6.1% (w/w) measured as total volatiles on a Sartorious IR at 115° C. The equivalent water activity was about 0.20 at 25° C. The obtained spray dried powder contained 1.2E+11 CFU/g ±15%, equivalent to a survival rate of 25%, compared to <0.1% when drying the same formulation on the same spray dryer at ambient pressure in air and with no cooling conveying gas.

EXAMPLES 10-15

Using the same set-up as in example 1, the strains listed in table 1 were dried. Additives as listed in table 2 were added. Conditions and results are listed in table 3.

TABLE 1

| Example No. | Strain |
| --- | --- |
| Ex10 | *Lactobacillus acidophilus* (LA-5 ®) |
| Ex11 | *Lactobacillus buchneri* (LB-1819) |
| Ex12 | *Lactobacillus reuteri* protectis (RC-14) |
| Ex13 | *Streptococcus thermophilus* (ST-143) |
| Ex14 | *Streptococcus thermophilus* (ST-44) |
| Ex15 | *Streptococcus thermophilus* (ST-4895) |

TABLE 2

| Example no | Casein hydrolysate | Inosine | Inosine-monophosphate | Inositol | Inulin | Lactose | Maltodextrin (12 DE) | MonoNa-glutaminate |
|---|---|---|---|---|---|---|---|---|
| Ex10 | | | | | | | X | |
| Ex11 | | | | | | | X | |
| Ex12 | | | | | | | X | |
| Ex13 | | X | | X | | | | X |
| Ex14 | | | X | X | | | | X |
| Ex15 | | X | | X | | | | X |

| Example no | Na-Alginate | Na-Ascorbate | Na-Caseinate | Skimmed milkpowder | Sucrose | Trehalose | Yeast extract |
|---|---|---|---|---|---|---|---|
| Ex10 | | X | | | X | | |
| Ex11 | | X | | | | X | X |
| Ex12 | | X | | | X | | |
| Ex13 | | X | X | | | | |
| Ex14 | | X | X | | | | |
| Ex15 | | X | X | | | | |

TABLE 3

| Example no | Solids content | Feed CFU/g | Vacuum kPa | Tin | Tout | Dried Product CFU/g | Water activity $a_w$ | Cell yield [%] | Mass yield [%] |
|---|---|---|---|---|---|---|---|---|---|
| Ex10 | 22 | 6.3E+10 | −0.40 | 70 | 35 | 1.4E+10 | 0.32 | 22 | 85 |
| Ex11 | 22 | 2.7E+10 | −0.37 | 80 | 37 | 1.4E+11 | 0.28 | 64 | 94 |
| Ex12 | 18 | 1.4E+11 | −0.39 | 70 | 35 | 7.1E+10 | 0.28 | 51 | 88 |
| Ex13 | 13 | 4.0E+10 | −0.37 | 70 | 35 | 5.6E+10 | 0.33 | 21 | 92 |
| Ex14 | 13 | 1.9E+10 | −0.38 | 100 | 45 | 2.7E+10 | 0.20 | 23 | 91 |
| Ex15 | 16 | 3.4E+11 | −0.37 | 80 | 38 | 5.0E+11 | 0.27 | 28 | 93 |

REFERENCES

EP1234019B1 (Danisco A/S)
U.S. Pat. No. 6,010,725A (Nestle SA)
Spray drying—Wikipedia, the free encyclopedia (27 Oct. 2014)

All references cited in this patent document are hereby incorporated herein in their entirety by reference.

The invention claimed is:

1. A process for removing liquid from a solution or suspension comprising a microorganism, comprising:
   (a) drying the suspension or solution by spraying the suspension or solution into a gas in a spray dryer at a gas inlet temperature between 50° C. and 200° C., the spray dryer having an outlet temperature of at most 70° C. and a pressure of between 15 kPa and 80 kPa, to obtain a dried material;
   (b) removing the dried material resulting from step (a) from the spray dryer, so that the dryer retention time of the material is less than 20 minutes in the spray dryer; and
   (c) conveying the dried material from step (b) to a separator by a cooling gas having a temperature below 30° C.

2. The process of claim 1, wherein the suspension or solution is an aqueous suspension comprising heat-labile microorganisms.

3. The process of claim 2, wherein step (a) comprises contacting droplets of the suspension containing the microorganisms with a drying gas in the spray dryer.

4. The process of claim 2, wherein the microorganism comprises lactic acid bacteria (LAB).

5. The process of claim 1, wherein step (b) is performed immediately after step (a).

6. The process of claim 5, wherein step (b) is performed using a cyclone that separates the dried material from the gas.

7. The process of claim 1, wherein the dryer retention time of the material is less than 2 minutes in the spray dryer.

8. The process of claim 1, wherein the drying step takes place at a temperature of between 10 and 60° C.

9. The process of claim 1, wherein the gas used in step (a) is selected from the group consisting of an inert gas, a noble gas, carbon dioxide, and an alkane gas, and a mixture of two or more thereof.

10. The process of claim 1, wherein the microorganism is selected from the group consisting of: a yeast, a lactic acid bacterium, a *Streptococcus* species, a *Lactobacillus* species, a *Lactococcus* species, a *Leuconostoc* species, a *Bifidobacterium* species, an Oenococcus species, and a *Bacillus* species.

11. The process of claim 1, wherein the cooling gas has a temperature in the range of 5° C. to 25° C.

12. The process of claim 1, wherein the drying step takes place at a temperature of between 20 and 50° C.

13. The process of claim 1, wherein the cooling gas has a temperature below 20° C.

14. The process of claim 1, further comprising (e) packaging the resulting product of step (c).

15. The process of claim 1, further comprising (d) subjecting the dried material from step (c) to a further drying step.

16. The process of claim 15, further comprising packaging the resulting product of step (d).

17. The process of claim 1, wherein the spray dryer has a pressure between 30 kPa and 70 kPa.

* * * * *